(12) United States Patent
Chen

(10) Patent No.: US 7,566,456 B2
(45) Date of Patent: Jul. 28, 2009

(54) ALLERGEN VACCINE PROTEINS FOR THE TREATMENT AND PREVENTION OF ALLERGIC DISEASES

(76) Inventor: Haiming Chen, 6722 Corie La., West Hills, CA (US) 91307

( * ) Notice: Subject to any disclaimer, the term of this patent is extended or adjusted under 35 U.S.C. 154(b) by 308 days.

(21) Appl. No.: 11/474,180

(22) Filed: Jun. 23, 2006

(65) Prior Publication Data

US 2006/0292138 A1 Dec. 28, 2006

Related U.S. Application Data

(60) Provisional application No. 60/694,022, filed on Jun. 23, 2005.

(51) Int. Cl.
| | |
|---|---|
| C07K 14/00 | (2006.01) |
| C07K 17/00 | (2006.01) |
| A61K 39/00 | (2006.01) |
| A61K 39/35 | (2006.01) |
| A61K 39/36 | (2006.01) |

(52) U.S. Cl. .............. 424/185.1; 424/192.1; 424/275.1; 530/350

(58) Field of Classification Search ........................ None
See application file for complete search history.

(56) References Cited

U.S. PATENT DOCUMENTS

| | | | | |
|---|---|---|---|---|
| 5,541,087 | A | 7/1996 | Lo et al. | 435/697 |
| 5,726,044 | A | 3/1998 | Lo et al. | 435/69.7 |
| 6,660,843 | B1 | 12/2003 | Feige et al. | 530/391.7 |
| 6,797,493 | B2 | 9/2004 | Sun et al. | 435/69.7 |
| 6,900,292 | B2 | 5/2005 | Sun et al. | 530/387.3 |
| 7,030,226 | B2 | 4/2006 | Sun et al. | 530/387.3 |
| 7,067,110 | B1 | 6/2006 | Gillies et al. | 424/1.49 |
| 7,265,208 | B2 * | 9/2007 | Saxon et al. | 530/387.1 |
| 2002/0081664 | A1 | 6/2002 | Lo et al. | 435/69.5 |
| 2003/0026779 | A1 | 2/2003 | Yu et al. | 424/85.4 |
| 2003/0064063 | A1 | 4/2003 | Saxon | 424/131.1 |
| 2003/0082190 | A1 | 5/2003 | Saxon et al. | 424/178.1 |
| 2003/0082749 | A1 | 5/2003 | Sun et al. | 435/70.21 |
| 2003/0105294 | A1 | 6/2003 | Gillies et al. | 530/351 |
| 2003/0144187 | A1 | 7/2003 | Dunstan et al. | 514/12 |
| 2004/0001853 | A1 | 1/2004 | George et al. | 424/189.1 |
| 2004/0053366 | A1 | 3/2004 | Lo et al. | 435/69.1 |
| 2004/0175824 | A1 | 9/2004 | Sun et al. | 435/326 |
| 2004/0198961 | A1 | 10/2004 | An et al. | 530/391.1 |
| 2004/0241817 | A1 | 12/2004 | Umana et al. | 435/193 |
| 2004/0259209 | A1 | 12/2004 | Sun et al. | 435/69.7 |
| 2004/0265973 | A1 | 12/2004 | Sun et al. | 435/69.5 |
| 2005/0002902 | A1 | 1/2005 | Yu et al. | 424/85.7 |
| 2005/0042729 | A1 | 2/2005 | Lo et al. | 435/69.1 |
| 2005/0124045 | A1 | 6/2005 | Sun et al. | 435/69.7 |
| 2005/0142642 | A1 | 6/2005 | Sun et al. | 435/69.7 |
| 2005/0192211 | A1 | 9/2005 | Gillies et al. | 514/8 |
| 2005/0202538 | A1 | 9/2005 | Gillies et al. | 435/69.7 |
| 2005/0261229 | A1 | 11/2005 | Gillies et al. | 514/44 |
| 2005/0281829 | A1 | 12/2005 | Hehir et al. | 424/160.1 |
| 2006/0228332 | A1 | 10/2006 | Gillies et al. | 424/85.6 |
| 2006/0234307 | A1 | 10/2006 | Feige et al. | 435/7.1 |
| 2006/0275282 | A1 | 12/2006 | Moore et al. | 424/103.1 |
| 2006/0275283 | A1 | 12/2006 | van Vlijmen et al. | 424/130.1 |

OTHER PUBLICATIONS

Lerner et al. 'Tapping the immunological repertoire to produce antibodies of predetermined specificity.' Nature 299:592-596, 1982.*
Zhu, D., et al., A novel human immunoglobulin Fcγ-Fcε bifunctional fusion protein inhibits FcεRI-mediated degranulation, *Nature Medicine* 8(5):518-521, May 2002.
Zhu, D., et al., A chimeric human-cat fusion protein blocks cat-induced allergy, *Nature Medicine* 11(4) 446-449, Apr. 2005.

* cited by examiner

*Primary Examiner*—Maher M Haddad
*Assistant Examiner*—Nora M Rooney
(74) *Attorney, Agent, or Firm*—Seed IP Law Group PLLC

(57) ABSTRACT

The present invention provides fusion proteins comprising an allergen sequence linked via an IgG hinge region to another polypeptide sequence capable of specifically binding to a native IgG inhibitory receptor containing an immune receptor tyrosine based inhibitory motif (ITIM). They are designed to cross-link an Fc receptor for IgE (e.g., FcεR1) and an IgG inhibitory receptor (e.g., FcγRIIb), thereby inhibiting the IgE-driven mediators released from mast cells and basophils. In addition, the present invention provides nucleic acid molecules encoding the fusion proteins, vectors and host cells for producing the fusion proteins, pharmaceutical compositions comprising the fusion proteins, and methods for ameliorating or reducing the risk of IgE-medicated allergic diseases.

2 Claims, 4 Drawing Sheets

SEQUENCE LISTING

<160> NUMBER OF SEQ ID NOS: 24

<210> SEQ ID NO 1
<211> LENGTH: 699
<212> TYPE: DNA
<213> ORGANISM: Homo sapiens

<400> SEQUENCE: 1

```
gagcccaaat cttgtgacaa aactcacaca tgcccaccgt gcccagcacc tgaactcctg      60
gggggaccgt cagtcttcct cttccccca aacccaagg acaccctcat gatctcccgg      120
acccctgagg tcacatgcgt ggtggtggac gtgagccacg aagaccctga ggtcaagttc      180
aactggtacg tggacggcgt ggaggtgcat aatgccaaga caaagccgcg ggaggagcag      240
tacaacagca cgtaccgggt ggtcagcgtc ctcaccgtcc tgcaccagga ctggctgaat      300
ggcaaggagt acaagtgcaa ggtctccaac aaagccctcc cagcccccat cgagaaaacc      360
atctccaaag ccaagggca gccccgagaa ccacaggtgt acaccctgcc cccatcccgg      420
gatgagctga ccaagaacca ggtcagcctg acctgcctgg tcaaaggctt ctatcccagc      480
gacatcgccg tggagtggga gagcaatggg cagccggaga acaactacaa gaccacgcct      540
cccgtgctgg actccgacgg ctccttcttc ctctacagca agctcaccgt ggacaagagc      600
aggtggcagc aggggaacgt cttctcatgc tccgtgatgc atgaggctct gcacaaccac      660
tacacgcaga agagcctctc cctgtctccg ggtaaatga               699
```

<210> SEQ ID NO 2
<211> LENGTH: 232
<212> TYPE: PRT
<213> ORGANISM: Homo sapiens

<400> SEQUENCE: 2

```
Glu Pro Lys Ser Cys Asp Lys Thr His Thr Cys Pro Pro Cys Pro Ala
  1               5                  10                  15

Pro Glu Leu Leu Gly Gly Pro Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

-continued

<210> SEQ ID NO 3
<211> LENGTH: 666
<212> TYPE: DNA
<213> ORGANISM: Dermatophagoides pteronyssinus

<400> SEQUENCE: 3

```
actaacgcct gcagtatcaa tggaaatgct ccagctgaaa tcgatttgcg acaaatgcga     60
actgtcactc ccattcgtat gcaaggaggc tgtggttcat gttgggcttt ctctggtgtt    120
gccgcaactg aatcagctta tttggcttac cgtaatcaat cattggatct tgctgaacaa    180
gaattagtcg attgtgcttc ccaacacggt tgtcatggtg ataccattcc acgtggtatt    240
gaatacatcc aacataatgg tgtcgtccaa gaaagctact atcgatacgt tgcacgagaa    300
caatcatgcc gacgaccaaa tgcacaacgt ttcggtatct caaactattg ccaaatttac    360
ccaccaaatg taaacaaaat tcgtgaagct ttggctcaaa cccacagcgc tattgccgtc    420
attattggca tcaaagattt agacgcattc cgtcattatg atggccgaac aatcattcaa    480
cgcgataatg gttaccaacc aaactatcac gctgtcaaca ttgttggtta cagtaacgca    540
caaggtgtcg attattggat cgtacgaaac agttgggata ccaattgggg tgataatggt    600
tacggttatt ttgctgccaa catcgatttg atgatgattg aagaatatcc atatgttgtc    660
attctc                                                               666
```

<210> SEQ ID NO 4
<211> LENGTH: 222
<212> TYPE: PRT
<213> ORGANISM: Dermatophagoides pteronyssinus

<400> SEQUENCE: 4

```
Thr Asn Ala Cys Ser Ile Asn Gly Asn Ala Pro Ala Glu Ile Asp Leu
 1               5                  10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala His Arg Asn Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Ala Asn Lys Ile Arg
        115                 120                 125

Glu Ala Leu Ala Gln Pro Gln Arg Tyr Cys Arg His Tyr Trp Thr Ile
    130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175
```

```
Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Glu Tyr Pro Tyr Val Val Ile Leu
    210                 215                 220

<210> SEQ ID NO 5
<211> LENGTH: 279
<212> TYPE: DNA
<213> ORGANISM: Felis catus

<400> SEQUENCE: 5 atgaagggggg ctcgtgttct cgtgcttctc tgggctgcct tgctcttgat ctggggtgga      60
aattgtgaaa tttgcccagc cgtgaagagg gatgttgacc tattcctgac gggaaccccc     120
gacgaatatg ttgagcaagt ggcacaatac aaagcactac ctgtagtatt ggaaaatgcc     180
agaatactga agaactgcgt tgatgcaaaa atgacagaag aggataagga gaatgctctc     240
agcttgctgg acaaaatata cacaagtcct ctgtgttaa                            279

<210> SEQ ID NO 6
<211> LENGTH: 92
<212> TYPE: PRT
<213> ORGANISM: Felis catus

<400> SEQUENCE: 6

Met Lys Gly Ala Arg Val Leu Val Leu Leu Trp Ala Ala Leu Leu Leu
  1               5                  10                  15

Ile Trp Gly Gly Asn Cys Glu Ile Cys Pro Ala Val Lys Arg Asp Val
             20                  25                  30

Asp Leu Phe Leu Thr Gly Thr Pro Asp Glu Tyr Val Glu Gln Val Ala
         35                  40                  45

Gln Tyr Lys Ala Leu Pro Val Val Leu Glu Asn Ala Arg Ile Leu Lys
     50                  55                  60

Asn Cys Val Asp Ala Lys Met Thr Glu Glu Asp Lys Glu Asn Ala Leu
 65                  70                  75                  80

Ser Leu Leu Asp Lys Ile Tyr Thr Ser Pro Leu Cys
                 85                  90

<210> SEQ ID NO 7
<211> LENGTH: 330
<212> TYPE: DNA
<213> ORGANISM: Felis catus

<400> SEQUENCE: 7
atgagggggg cactgcttgt gctggcattg ctggtgaccc aagcgctggg cgtcaagatg       60
gcggaaactt gccccatttt ttatgacgtc tttttttgcgg tggccaatgg aaatgaatta     120
ctgttggact tgtccctcac aaaagtcaat gctactgaac agagagaac agccatgaaa       180 aaaatccagg attgctacgt ggagaacgga ctcatatcca gggtcttgga tggactagtc     240
atgcaaacca tcagctccag caaagattgc atgggtgaag cagttcagaa caccgtagaa     300
gatctcaagc tgaacacttt ggggagataa                                      330

<210> SEQ ID NO 8
<211> LENGTH: 109
<212> TYPE: PRT
<213> ORGANISM: Felis catus
```

```
<400> SEQUENCE: 8

Met Arg Gly Ala Leu Leu Val Leu Ala Leu Leu Val Thr Gln Ala Leu
 1               5                  10                  15

Gly Val Lys Met Ala Glu Thr Cys Pro Ile Phe Tyr Asp Val Phe Phe
            20                  25                  30

Ala Val Ala Asn Gly Asn Glu Leu Leu Asp Leu Ser Leu Thr Lys
        35                  40                  45

Val Asn Ala Thr Glu Pro Glu Arg Thr Ala Met Lys Lys Ile Gln Asp
50                  55                  60

Cys Tyr Val Glu Asn Gly Leu Ile Ser Arg Val Leu Asp Gly Leu Val
65                  70                  75                  80

Met Thr Thr Ile Ser Ser Ser Lys Asp Cys Met Gly Glu Ala Val Gln
                85                  90                  95

Asn Thr Val Glu Asp Leu Lys Leu Asn Thr Leu Gly Arg
                100                 105

<210> SEQ ID NO 9
<211> LENGTH: 1878
<212> TYPE: DNA
<213> ORGANISM: Arachis hypogaea

<400> SEQUENCE: 9
atgagaggga gggtttctcc actgatgctg ttgctaggga tccttgtcct ggcttcagtt      60
tctgcaacgc atgccaagtc atcaccttac cagaagaaaa cagagaaccc ctgcgcccag     120
aggtgcctcc agagttgtca acaggaaccg atgacttga agcaaaaggc atgcgagtct     180
cgctgcacca agctcgagta tgatcctcgt tgtgtctatg atcctcgagg acacactggc     240
accaccaacc aacgttcccc tccaggggag cggacacgtg ccgccaaccc ggagactac     300 gatgatgacc gccgtcaacc ccgaagagag gaggaggcc gatggggacc agctggaccg     360
agggagcgtg aaagagaaga agactggaga caaccaagaa aagattggag cgaccaagt     420 catcagcagc cacggaaaat aaggcccgaa ggaagagaag gagaacaaga gtggggaaca     480
ccaggtagcc atgtgaggga agaaacatct cggaacaacc ctttctactt cccgtcaagg     540
cggtttagca cccgctacgg gaaccaaaac ggtaggatcc gggtcctgca gaggtttgac     600
caaaggtcaa ggcagtttca gaatctccag aatcaccgta ttgtgcagat cgaggccaaa     660
cctaacactc ttgttcttcc caagcacgct gatgctgata catccttgt tatccagcaa     720 ggcaagccac cgtgaccgta gcaaatggca ataacagaaa gagctttaat cttgacgagg     780
gccatgcact cagaatccca tccggtttca tttcctacat cttgaaccgc atgacaacc     840 agaacctcag agtagctaaa atctccatgc ccgttaacac acccggccag tttgaggatt     900
tcttcccggc gagcagccga gaccaatcat cctacttgca gggcttcagc aggaatacgt     960
tggaggccgc cttcaatgcg gaattcaatg agatacggag ggtgctgtta gaagagaatg    1020
caggaggtga gcaagaggag agagggcaga ggcgatggga tactcggagt agtgagaaca    1080
atgaaggagt gatagtcaaa gtgtcaaagg agcacgttga gaacttact aagcacgcta    1140 aatccgtctc aaagaaaggc tccgaagaag agggagatat caccaaccca atcaacttga    1200
gagaaggcga gcccgatctt tctaacaact ttgggaagtt atttgaggtg aagccagaca    1260
agaagaaccc ccagcttcag gacctggaca tgatgctcac ctgtgtagag atcaagaag    1320 gagctttgat gctcccacac ttcaactcaa aggccatggt tatcgtcgtc gtcaacaaag    1380
gaactggaaa ccttgaactc gtggctgtaa gaaaagagca acaacagagg ggacggcggg    1440
```

```
aagaagagga ggacgaagac gaagaagagg agggaagtaa cagagaggtg cgtaggtaca    1500
cagcgaggtt gaaggaaggc gatgtgttca tcatgccagc agctcatcca gtagccatca    1560
acgcttcctc cgaactccat ctgcttggct tcggtatcaa cgctgaaaac aaccacagaa    1620
tcttccttgc aggtgataag gacaatgtga tagaccagat agagaagcaa gcgaaggatt    1680
tagcattccc tgggtcgggt gaacaagttg agaagctcat caaaaaccag aaggaatctc    1740
actttgtgag tgctcgtcct caatctcaat ctcaatctcc gtcgtctcct gagaaagagt    1800
ctcctgagaa agaggatcaa gaggaggaaa accaaggagg gaagggtcca ctcctttcaa    1860
ttttgaaggc ttttaact                                                   1878

<210> SEQ ID NO 10
<211> LENGTH: 626
<212> TYPE: PRT
<213> ORGANISM: Arachis hypogaea

<400> SEQUENCE: 10

Met Arg Gly Arg Val Ser Pro Leu Met Leu Leu Gly Ile Leu Val
 1               5                  10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285
```

```
Ser Met Pro Val Asn Thr Pro Gly Gln Phe Glu Asp Phe Pro Ala
290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
                340                 345                 350

Trp Ser Thr Arg Ser Ser Glu Asn Asn Glu Gly Val Ile Val Lys Val
                355                 360                 365

Ser Lys Glu His Val Glu Glu Leu Thr Lys His Ala Lys Ser Val Ser
370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
                420                 425                 430

Leu Thr Cys Val Glu Ile Lys Glu Gly Ala Leu Met Leu Pro His Phe
                435                 440                 445

Asn Ser Lys Ala Met Val Ile Val Val Asn Lys Gly Thr Gly Asn
450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
                500                 505                 510

Pro Ala Ala His Pro Val Ala Ile Asn Ala Ser Ser Glu Leu His Leu
                515                 520                 525

Leu Gly Phe Gly Ile Asn Ala Glu Asn Asn His Arg Ile Phe Leu Ala
                530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
                580                 585                 590

Ser Pro Ser Ser Pro Glu Lys Glu Ser Pro Glu Lys Glu Asp Gln Glu
                595                 600                 605

Glu Glu Asn Gln Gly Gly Lys Gly Pro Leu Leu Ser Ile Leu Lys Ala
                610                 615                 620

Phe Asn
625

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
ggggatccga gcccaaatct tgtgac                                          26
```

```
<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gtgcggccgc tcatttaccc ggagacaggg agag                                    34

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ggcccagccg gccgaaattt gcccagccgt g                                       31

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ggatcctctc cccaaagtgt tcag                                               24

<210> SEQ ID NO 15
<211> LENGTH: 914
<212> TYPE: DNA
<213> ORGANISM: Homo sapiens

<400> SEQUENCE: 15
gagcccaaat cttgtgacaa aactcacaca tgcccaccgt gcccaggtaa gccagcccag        60
gcctcgccct ccagctcaag gcgggacagg tgccctagag tagcctgcat ccagggacag       120
gccccagccg ggtgctgaca cgtccacctc catctcttcc tcagcacctg aactcctggg       180
gggaccgtca gtcttcctct tccccccaaa acccaaggac accctcatga tctcccggac       240
ccctgaggtc acatgcgtgg tggtggacgt gagccacgaa gaccctgagg tcaagttcaa       300
ctggtacgtg gacggcgtgg aggtgcataa tgccaagaca aagccgcggg aggagcagta       360
caacagcacg taccgtgtgg tcagcgtcct caccgtcctg caccaggact ggctgaatgg       420
caaggagtac aagtgcaagg tctccaacaa agccctccca gcccccatcg agaaaaccat       480
ctccaaagcc aaaggtggga cccgtggggt gcgagggcca catggacaga ggccggctcg       540
gcccaccctc tgccctgaga gtgaccgctg taccaacctc tgtccctaca gggcagcccc       600
gagaaccaca ggtgtacacc ctgcccccat cccgggatga gctgaccaag aaccaggtca       660
gcctgacctg cctggtcaaa ggcttctatc ccagcgacat cgccgtggag tgggagagca       720
atgggcagcc ggagaacaac tacaagacca cgcctcccgt gctggactcc gacggctcct       780
tcttcctcta cagcaagctc accgtggaca agagcaggtg gcagcagggg aacgtcttct       840
catgctccgt gatgcatgag gctctgcaca accactacac gcagaagagc ctctccctgt       900
ctccgggtaa atga                                                         914
```

<210> SEQ ID NO 16
<211> LENGTH: 1541
<212> TYPE: DNA
<213> ORGANISM: Artificial Sequence
<220> FEATURE:
<223> OTHER INFORMATION: Nucleotide sequence encoding katcin fusion protein

<400> SEQUENCE: 16

```
atggagacag acacactcct gctatgggta ctgctgctct gggttccagg ttccactggt    60
gacgcggccc agccggccga aatttgccca gccgtgaaga gggatgttga cctattcctg    120
acgggaaccc ccgacgaata tgttgagcaa gtggcacaat acaaagcact acctgtagta    180
ttggaaaatg ccagaatact gaagaactgc gttgatgcaa aaatgacaga agaggataag    240
gagaatgctc tcagcttgct ggacaaaata tacacaagtc ctctgtgtca tatgggtgga    300
ggaggttctg gtggaggagg ttctggtgga ggaggttctc tgcaggtcaa gatggcggaa    360
acttgcccca ttttttatga cgtctttttt gcggtggcca atggaaatga attactgttg    420
gacttgtccc tcacaaaagt caatgctact gaaccagaga aacagccat gaaaaaaatc    480
caggattgct acgtggagaa cggactcata tccagggtct ggatggact agtcatgaca    540
accatcagct ccagcaaaga ttgcatgggt gaagcagttc agaacaccgt gaagatctc    600
aagctgaaca ctttggggag aggatccgag cccaaatctt gtgacaaaac tcacacatgc    660
ccaccgtgcc caggtaagcc agcccaggcc tcgccctcca gctcaaggcg ggacaggtgc    720
cctagagtag cctgcatcca gggacaggcc cagccgggt gctgacacgt ccacctccat    780
ctcttcctca gcacctgaac tcctgggggg accgtcagtc ttcctcttcc ccccaaaacc    840
caaggacacc ctcatgatct cccggacccc tgaggtcaca tgcgtggtgg tggacgtgag    900
ccacgaagac cctgaggtca agttcaactg gtacgtggac ggcgtggagg tgcataatgc    960
caagacaaag ccgcgggagg agcagtacaa cagcacgtac cgtgtggtca gcgtcctcac    1020
cgtcctgcac caggactggc tgaatggcaa ggagtacaag tgcaaggtct ccaacaaagc    1080
cctcccagcc cccatcgaga aaaccatctc caaagccaaa ggtgggaccc gtgggtgcg    1140
agggccacat ggacagaggc cggctcggcc caccctctgc cctgagagtg accgctgtac    1200
caacctctgt ccctacaggg cagccccgag aaccacaggt gtacaccctg ccccatccc    1260
gggatgagct gaccaagaac caggtcagcc tgacctgcct ggtcaaaggc ttctatccca    1320
gcgacatcgc cgtggagtgg gagagcaatg ggcagccgga gaacaactac aagaccacgc    1380
ctcccgtgct ggactccgac ggctccttct cctctacag caagctcacc gtggacaaga    1440
gcaggtggca gcaggggaac gtcttctcat gctccgtgat gcatgaggct ctgcacaacc    1500
actacacgca gaagagcctc tccctgtctc cgggtaaatg a    1541
```

<210> SEQ ID NO 17
<211> LENGTH: 441
<212> TYPE: PRT
<213> ORGANISM: Artificial Sequence
<220> FEATURE:
<223> OTHER INFORMATION: Amino acid sequence of katcin fusion protein

<400> SEQUENCE: 17

```
Met Glu Thr Asp Thr Leu Leu Leu Trp Val Leu Leu Leu Trp Val Pro
 1               5                  10                  15

Gly Ser Thr Gly Asp Ala Ala Gln Pro Ala Glu Ile Cys Pro Ala Val
                20                  25                  30
```

```
Lys Arg Asp Val Asp Leu Phe Leu Thr Gly Thr Pro Asp Glu Tyr Val
         35                  40                  45

Glu Gln Val Ala Gln Tyr Lys Ala Leu Pro Val Val Leu Glu Asn Ala
 50                  55                  60

Arg Ile Leu Lys Asn Cys Val Asp Ala Lys Met Thr Glu Glu Asp Lys
 65                  70                  75                  80

Glu Asn Ala Leu Ser Leu Leu Asp Lys Ile Tyr Thr Ser Pro Leu Cys
                 85                  90                  95

His Met Gly Gly Gly Ser Gly Gly Gly Ser Gly Gly Gly Gly
                100                 105                 110

Ser Leu Gln Val Lys Met Ala Glu Thr Cys Pro Ile Phe Tyr Asp Val
        115                 120                 125

Phe Phe Ala Val Ala Asn Gly Asn Glu Leu Leu Leu Asp Leu Ser Leu
130                 135                 140

Thr Lys Val Asn Ala Thr Glu Pro Glu Arg Thr Ala Met Lys Lys Ile
145                 150                 155                 160

Gln Asp Cys Tyr Val Glu Asn Gly Leu Ile Ser Arg Val Leu Asp Gly
                165                 170                 175

Leu Val Met Thr Thr Ile Ser Ser Lys Asp Cys Met Gly Glu Ala
                180                 185                 190

Val Gln Asn Thr Val Glu Asp Leu Lys Leu Asn Thr Leu Gly Arg Gly
        195                 200                 205

Ser Glu Pro Lys Ser Cys Asp Lys Thr His Thr Cys Pro Pro Cys Pro
        210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
                275                 280                 285

Gln Tyr Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
                340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440
```

<210> SEQ ID NO 18
<211> LENGTH: 70
<212> TYPE: PRT
<213> ORGANISM: Felis catus

<400> SEQUENCE: 18

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
    50                  55                  60

Tyr Thr Ser Pro Leu Cys
65                  70

<210> SEQ ID NO 19
<211> LENGTH: 92
<212> TYPE: PRT
<213> ORGANISM: Felis catus

<400> SEQUENCE: 19

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Thr Thr Ile Ser Ser Lys Asp Cys Met Gly Glu Ala Val Gln Asn
65                  70                  75                  80

Thr Val Glu Asp Leu Lys Leu Asn Thr Leu Gly Arg
                85                  90

<210> SEQ ID NO 20
<211> LENGTH: 15
<212> TYPE: PRT
<213> ORGANISM: Homo sapiens

<400> SEQUENCE: 20

Glu Pro Lys Ser Cys Asp Lys Thr His Thr Cys Pro Pro Cys Pro
1               5                   10                  15

<210> SEQ ID NO 21
<211> LENGTH: 217
<212> TYPE: PRT
<213> ORGANISM: Homo sapiens

<400> SEQUENCE: 21

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 22
<211> LENGTH: 12
<212> TYPE: PRT
<213> ORGANISM: Homo sapiens

<400> SEQUENCE: 22

Glu Arg Lys Cys Cys Val Glu Cys Pro Pro Cys Pro
 1               5                  10

<210> SEQ ID NO 23
<211> LENGTH: 62
<212> TYPE: PRT
<213> ORGANISM: Homo sapiens

<400> SEQUENCE: 23

Glu Leu Lys Thr Pro Leu Gly Asp Thr Thr His Thr Cys Pro Arg Cys
 1               5                  10                  15

Pro Glu Pro Lys Ser Cys Asp Thr Pro Pro Cys Pro Arg Cys Pro
             20                  25                  30

Glu Pro Lys Ser Cys Asp Thr Pro Pro Cys Pro Arg Cys Pro Glu
         35                  40                  45

Pro Lys Ser Cys Asp Thr Pro Pro Cys Pro Arg Cys Pro
     50                  55                  60

<210> SEQ ID NO 24
<211> LENGTH: 12
<212> TYPE: PRT
<213> ORGANISM: Homo sapiens

<400> SEQUENCE: 24

Glu Ser Lys Tyr Gly Pro Pro Cys Pro Ser Cys Pro
 1               5                  10
```

ALLERGEN VACCINE PROTEINS FOR THE TREATMENT AND PREVENTION OF ALLERGIC DISEASES

CROSS-REFERENCE TO RELATED APPLICATION

This application claims the benefit under 35 USC 119(e) of U.S. Provisional Patent Application No. 60/694,022, filed Jun. 23, 2005, where this provisional application is incorporated herein by reference in its entirety.

BACKGROUND OF THE INVENTION

1. Field of the Invention

The present invention relates to allergen vaccines, and more particularly to allergen vaccines that utilize fusion proteins in the treatment and prevention of allergic diseases.

2. Description of the Related Art

An allergy is an immune system reaction to a typically harmless substance. The immune system is always working to fight off parasites, fungi, viruses and bacteria. However, sometimes the immune system will treat a harmless substance (called an allergen) as an unwanted invader and try to fight it. This overreaction of the body's immune system to a typically harmless substance is called an allergic reaction.

Different allergies have different names, according to where they occur in the body. There are five common types of allergies, namely, allergic rhinitis, allergic dermatitis, asthma, food allergies and urticaria.

Allergic rhinitis affects the eyes, nose and sinuses. It causes stuffy or runny nose, ears and throat postnasal, watery or itchy eyes, and bronchial tube irritation, also known as hay fever. Allergic dermatitis affects the skin, causing an itchy rash. It is also known as contact dermatitis. Asthma affects the lungs, causing shortness of breath or wheezing. Food allergies affect the stomach and other internal organs, and may also cause symptoms to the entire body. Urticaria is a condition resulting with hives on the skin.

Almost anything can act as an allergen. However, some substances are very common allergens, such as, pollen and mold, dust mite droppings, pet allergens, food allergies, insect stings, and cockroach sensitivities. About a quarter of all Americans are genetically predisposed to allergic reactions from airborne pollen and mold. Dust mites, which are tiny spider-like creatures, leave droppings on bedsheets, pillows, and furniture. It is found that at least twenty million Americans are allergic to dust mite droppings, making it the next most common allergen. Around fifteen to thirty percent of people with allergies are found to be allergic to the third most popular allergens, pet allergens. They are sensitive to the proteins in pet dander (dead skin), pet saliva and pet urine. Those with dog allergies may be allergic to all dogs, or just certain breeds, but those with cat allergies are generally allergic to all cats. Cat allergies are about twice as common as dog allergies, affecting about six to ten million Americans.

Sensitivities to certain foods affect three to eight percent of children and one to two percent of adults. Ninety percent of all food allergies are caused by eight types of food, namely, milk, soy, eggs, wheat, peanuts, tree nuts, fish and shellfish. A few food preservatives also cause allergic reactions, namely, monosodium glutamate (found in many Asian foods, bouillon cubes and other preserved meat products) and metabisulfites (found in wines, particularly red wines). Insect stings from bees, wasps, fire ants, and the like, can be life threatening, and about two million Americans are prone to these allergic reactions. The toxins from the sting can cause severe reactions ranging from hives, wheezing, itching, swelling of the tongue, or even cardiac arrest. Cockroach sensitivies result when a cockroach crawls over food, or when cockroach droppings become airborne, and such allergens are ingested or inhaled, causing an allergic reaction. Anywhere from twenty-three to sixty percent of urban asthma sufferers are allergic to cockroach allergens.

It is important to realize that allergies are not only troublesome during the pollen season, but can be debilitating and become chronic disorders, which can have a negative long-term effect on one's health, pocketbook and happiness. Allergies should be taken seriously, and it is important to learn more about it.

Many allergies are passed onto children genetically through their parents. There is a one in three chance of developing some sort of allergy if the parent has the allergy (although not necessarily to the same allergen), according to the Asthma and Allergy Foundation of America. And if both parents have allergies, the child has a seventy percent chance of developing allergies. The substances that a person is allergic to depend on one's own genetic makeup, as well as one's exposure. Another factor is age. It was found that the peak age for developing an allergy seems to be around age nineteen.

One type of allergic reaction that requires special attention is anaphylaxis, which is sudden, severe, and potentially fatal, with symptoms that can affect various areas of the body. The symptoms usually appear very quickly after exposure to the allergen and can include intense itching all over the body, full-body swelling, respiratory distress, and can even lead to life threatening shock.

These reactions demand prompt medical attention and may require not only antihistamines and corticosteroids for relief, but also a form of adrenaline known as epinephrine. People who are highly susceptible to anaphylactic reactions should always carry a syringe of epinephrine with them and wear a medical alert bracelet.

A hallmark of the allergic diathesis is the tendency to maintain a persistent IgE response after antigen (allergen) presentation. The initial exposure to antigens stimulates the production of specific IgE molecules, which bind to high-affinity Fc receptors on the surface of mast cells. Upon reexposure of antigens, the cross-linking of antigens and membrane-bound IgE molecules result in the release of vasoactive mediators, setting off subsequent clinical manifestation of sneezing, pruritus, and bronchospasm. Immunoglobulin receptors (also referred to as Fc receptors), are cell-surface receptors of mast cells, that bind to the constant region of immunoglobulins, and mediate various immunoglobulin functions other than antigen binding.

Fc receptors that bind with IgE molecules (a type of immunoglobulin) are found on many types of cells in the immune system. There are two different Fc receptors currently known for IgE, the multichain high-affinity receptor, FcεRI, and the low-affinity receptor, FcεRII. IgE molecules mediate its biological responses as an antibody through these Fc receptors. The high-affinity FcεRI receptor, expressed on the surface of mast cells, basophils, and Langerhans cells, belongs to the immunoglobulin gene superfamily, and has a tetrametric structure composed of an α-chain, a β-chain and two disulfide-linked γ-chains that are required for receptor expression and signal transduction. The α-chains of the receptor interact with the distal portion of the third constant domain of the IgE heavy chain. The specific region of the human IgE molecule involved in binding to the human FcεRI receptor have been identified as including six amino acids, Arg-408, Ser-411, Lys-415, Glu-452, Arg-465, and Met-469. The interaction is highly specific with a binding constant of about $10^{10} M^{-1}$.

The low-affinity FcεRII receptor, represented on the surface of inflammatory cells, such as eosinophils, leukocytes, B lymphocytes, and platelets, did not evolve from the immunoglobulin superfamily but has substantial homology with several groups of animals and is made up of a transmembrane chain with an intracytoplasmic $NH_2$ terminus. The low-affinity receptor, FcεRII (CD23), is currently known to have two forms, FcεRIIa and FcεRIIb, both of which have been cloned and sequenced. The two forms differ only in the N-terminal cytoplasmic region, with the extracellular domains being identical. FcεRIIa is normally expressed on B cells, while FcεRIIb is expressed on T cells, B cells, monocytes and eosinophils upon induction by the cytokine IL-4.

Through the high-affinity FcεRI receptor, IgE plays key roles in an array of acute and chronic allergic reactions, including asthma, allergic rhinitis, atopic dermatitis, severe food allergies, chronic urticaria and angioedema, as well as the serious physiological condition of anaphylactic shock. The binding of a multivalent antigen to an antigen-specific IgE molecule, which is specifically bound to a FcεRI receptor on the surface of a mast cell or basophil, stimulates a complex series of signaling events that culminate in the release of host vasoactive and proinflammatory mediators that contributes to both acute and late-phase allergic responses.

The function of the low-affinity FcεRII receptor (also referred to as CD23), found on the surface of B lymphocytes, is less well-established than that of the FcεRI receptor. FcεRII, in a polymeric state, binds to IgE molecules, and this binding may play a role in controlling the type (class) of antibody produced by B cells.

Three groups of Fcγ receptors that bind to the constant region of human IgG molecules have so far been identified on cell surfaces. They are, FcγRI (CD64), FcγRII (CD32), and FcγRIII (CD16), all of which belong to the immunoglobulin gene superfamily. The three Fcγ receptors have a large number of various isoforms.

In addition to the stimulatory FcεRI receptor, mast cells and basophils also co-express an immunoreceptor tyrosine-based inhibition motif (ITIM)-containing inhibitory low-affinity receptor, called the FcγRIIb receptor, which act to negatively regulate antibody functions. The FcγRIIb receptor belongs in the inhibitory receptor superfamily (IRS), which is a growing family of structurally and functionally similar inhibitory receptors that negatively regulate immunoreceptor tyrosine-based activation motif (ITAM)-containing immune receptors and a diverse array of other cellular responses. Coaggregation of an IRS member (such as FcγRIIb receptor) with an activating receptor (such as FcεRI receptor) leads to phosphorylation of the characteristic ITIM tyrosine and subsequent recruitment of the SH2 domain-containing protein tyrosine phosphatases SHP-1 and SHP-2, and the SH2 domain-containing phospholipases, SHIP and SHIP2. Possible outcomes of the coaggregation include inhibition of cellular activation, as demonstrated by the coaggregation of FcγRIIb and B-cell receptors, T-cell receptors, and activating receptors, such as FcεRI and cytokine.

A key contributor to asthma, allergic rhinitis and severe food reactions is the induced IgE-driven mediators released from mast cells and basophils. The cross-linking of a mast cell or basophil FcεRI receptor with a multivalent antigen, activates tyrosine phosphorylation of immunoreceptor tyrosine-based activation motifs (ITAMs) in the β- and γ-FcεRI subunit cytoplasmic tails, thereby initiating downstream signaling through Syk. Mast cells and basophils also express the FcγRIIb receptor, which contains a single conserved immunoreceptor tyrosine-based inhibition motif (ITIM) within its cytoplasmic tail. Studies indicate that the aggregating of FcγRIIb to FcεRI leads to rapid tyrosine phosphorylation of the FcγRIIb ITIM tyrosine by FcεRI-associated Lyn and inhibition of FcεRI signaling. This hypothesis has been supported in experiments using human Ig Fcγ-Fcε fusion proteins that directly cross-link the FcεRI and FcγRIIb receptors on human basophils.

Treatments of allergies include avoidance, immunotherapy, and allergy medications. The best course may simply be avoiding any allergens. Minimizing exposure can make a significant difference to allergy sufferers. However complete avoidance is not always possible.

Immunotherapy, also known as allergy shots, can help built allergy resistance. However immunotherapy is expensive and may take several years to take effect on the allergies. For most allergy sufferers, medications that treat allergy symptoms are a much better option.

Allergy medications can sometimes control the symptoms with over-the-counter or prescription medications. The treatment of allergy such as severe asthma is still a serious medical challenge. In addition, many of the therapeutics currently used in allergy treatment have serious side-effects. Common allergy medications include corticosteroids, steroid nasal sprays, antihistamines, decongestants, decongestants combined with antihistamines, cromolyn sodium and ipratropium bromide.

Doctors and allergy sufferers are anxiously awaiting the FDA to approve an Anti-IgE compound called omalizumab (brand name Xolair) for the treatment of allergic asthma. Omalizumab is the first anti-IgE drug submitted for FDA approval, although more are on the horizon.

Anti-IgE drugs are a breakthrough in allergy treatment for those with severe year-round allergies. Basically, the antibody contained in anti-IgE drugs binds to the IgE circulating in the body after exposure to an allergen. This binding of the medication with the IgE prevents and the IgE from binding to mast cells and triggering mast cell rupture. The mast cells then remain intact, preventing the release of the histamine, prostaglandins and leukotrienes that cause allergy symptoms. In other words, instead of treating symptoms after they've already occurred. Anti-IgE drugs will prevent symptoms from occurring at all.

When approved, anti-IgE injections are expected to eventually replace traditional allergy immunotherapy injections. They offer a distinct advantage over traditional shots. Instead of doctors having to diagnose allergies precisely and administer specific solutions of those antibodies, anyone suffering from allergies can get a standard anti-IgE shot which will work to prevent allergic reactions, no matter what type. There are some side effects and very expensive.

Some prescription medications are avoidable to help control allergic rhinitis symptoms such as nasal steroids, antihistamines, and decongestants. But one of the newest forms of treatment for allergic rhinitis getting positive feedback are leukotrienses modifiers.

Leukotriene modifiers are not exactly new. But these drugs, originally approved to fight asthma, are proving effective in combating allergic rhinitis symptoms as well and are now being approved for that purpose.

Luekotriene modifier work by blocking the effects of leukotrienes, which are chemicals produced by certain cells in the body in response to an allergy. These leukotriene molecules contribute to the inflammation, swelling, airway constriction and production of mucus seen in allergic reactions. Leukotriene modifiers, which show a low incidence of side effects, are often prescribed in combination which steroids to prevent and treat allergy and asthma symptoms. In many cases, leukotriene modifiers help patients reduce their steroids dosage and help control symptoms such as itching, sneezing, wheezing and congestion.

Most US allergy sufferers who choose allergy immunotherapy treatment receive injections in their doctor's office. But an alternative therapy is getting good results in Europe. Instead of injections, allergy sufferers in France, Italy and Germany are prescribed allergen extract drops, which are concentrated dosages of the substance to which they are allergic, such as pollen. Allergy sufferers can place the drops under their tongue at home instead of visiting the doctor's office for shots.

The treatment is considered effective at controlling symptoms like wheezing, sneezing and runny noses that in Europe the French health care system use it for the treatment. Some American doctors are already using the drops system as well. But most American allergy sufferers will have to wait for FDA approval of the drops. The FDA is waiting for the results of ongoing studies of the drops before it initiates a formal review.

Although an anti-IgE antibody currently in clinical trials (rhuMAb-E26, Genentech, Inc.) and other experimental therapies such as antagonists of IL-4 show promising results, there is a need for the development of additional therapeutic strategies and agents to control allergic disease, such as asthma, severe food allergy, and chronic urticaria and angioedema.

One approach to the treatment of allergic diseases is by use of allergen-based immunotherapy. This methodology uses whole antigens as "allergy vaccine" and is now appreciated to induce a state of relative allergic tolerance. This technique for the treatment of allergy is frequently termed "desensitization" or "hyposensitization" therapy.

Increasing doses of allergic peptide are administered, typically by injection, to a subject over an extended period of time, frequently months or years. The mechanism of action of this therapy is thought to involve induction of IgG inhibitory antibodies, suppression of mast cell/basophil reactivity, the promotion of T-cell anergy, and/or clonal deletion, and in the long term, decrease in the levels of allergen specific IgE. The use of this approach is, however, hindered in many instances by poor efficacy and serious side effects including the risk of triggering a systemic and potentially fatal anaphylactic response, where the clinical administration of the allergen induces the severe allergic response it seeks to suppress. Thus, there exists a strong need to develop treatments for allergic diseases.

BRIEF SUMMARY OF THE INVENTION

The present invention provides fusion proteins that comprise an allergen sequence linked via an IgG hinge region to another polypeptide sequence capable of specifically binding to a native IgG inhibitory receptor containing an immune receptor tyrosine based inhibitory motif (ITIM). They are designed to cross-link an Fc receptor for IgE (e.g., FcεR1) and an IgG inhibitory receptor (e.g., FcγRIIb), thereby inhibiting the IgE-driven mediators released from mast cells and basophils (e.g., during the presentation of allergens). In addition, the present invention provides nucleic acid molecules encoding the fusion proteins, vectors and host cells for producing the fusion proteins, pharmaceutical compositions comprising the fusion proteins, and methods for ameliorating or reducing the risk of IgE-medicated allergic diseases.

In one aspect, the present invention provides a fusion protein comprising (i) a first polypeptide sequence capable of specifically binding to a native IgE molecule, (ii) a second polypeptide sequence capable of specifically binding to a native IgG inhibitory receptor comprising an immune receptor tyrosine based inhibitory motif (ITIM), and (iii) an IgG hinge region, wherein the first polypeptide sequence comprises an allergen sequence, and wherein the first polypeptide sequence and the second polypeptide sequence is functionally connected via the IgG hinge region.

In certain embodiments, the allergen sequence within the fusion protein is native cat allergen Fel d1 or a portion thereof. For example, the allergen sequence may comprise both a portion of native cat allergen Fel d1 chain 1 as set forth in SEQ ID NO:18 and a portion of native cat allergen Fel d1 chain 2 as set forth in SEQ ID NO:19.

In certain embodiments, the allergen sequence within the fusion protein is native mite allergen protein Der p1 as set forth in SEQ ID NO:4 or a portion thereof.

In certain embodiments, the allergen sequence within the fusion protein is native peanut allergen Ara has set forth in SEQ ID NO:10 or a portion thereof.

In certain embodiments, the IgG hinge region within the fusion protein is human IgG1 hinge region as set forth in SEQ ID NO:20.

In certain embodiments, the second polypeptide sequence is capable of specifically binding to a low-affinity IgG receptor FcγRIIb.

In certain embodiments, the second polypeptide within the fusion comprises the CH2 and CH3 portion of an IgG immunoglobulin heavy chain constant region. For example, the second polypeptide may comprise the CH2 and CH3 portion of human IgG1 immunoglobulin heavy chain constant region as set forth in SEQ ID NO:21.

In certain embodiments, the fusion protein is the protein referred to as "kitcin," which has the amino acid sequence as set forth in SEQ ID NO:17.

In another aspect, the present invention provides nucleic acid molecules comprising nucleotide sequences encoding the fusion proteins described herein.

In certain embodiments, the nucleic acid molecule comprises a nucleotide sequence that encodes the kitcin fusion protein having the amino acid sequence as set forth in SEQ ID NO:17. For example, in certain embodiments, the nucleic acid molecule comprises the nucleotide sequence as set forth in SEQ ID NO:16.

In certain embodiments, the present invention provides vectors comprising and capable of expressing the nucleotide sequence encoding the fusion protein described herein.

In certain embodiments, the vector comprises and is capable of the nucleotide sequence encoding the katcin fusion protein as set forth in SEQ ID NO:17. For example, in certain embodiments, the vector comprises the nucleotide sequence as set forth in SEQ ID NO:16.

In another aspect, the present invention provides host cells transformed with the vectors described herein.

In another aspect, the present invention provides pharmaceutical compositions comprising a fusion protein described herein and a pharmaceutically acceptable ingredient.

In another aspect, the present invention provides methods for ameliorating or reducing the risk of an IgE-mediated allergic disease, comprising administering to a patient in need thereof an effective amount of a fusion protein described herein.

BRIEF DESCRIPTION OF THE DRAWINGS

FIG. 1 illustrates an exemplary generic structure of an allergen vaccine protein.

FIG. 2 illustrates the structure of an exemplary mite allergen vaccine protein.

FIG. 3 illustrates the structure of an exemplary cat allergen vaccine protein.

Figure 7:
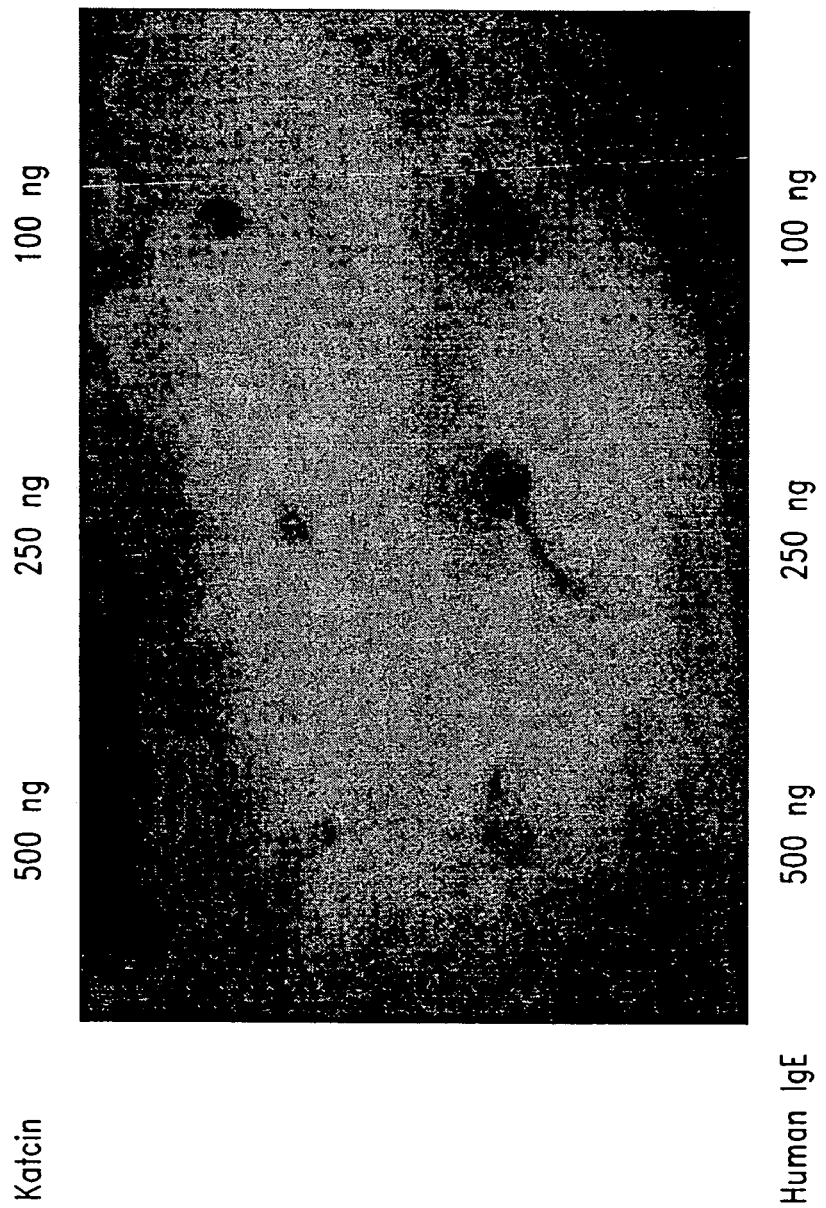

FIG. 7 is a photograph that shows the results of a passive cutaneous anaphylaxis analysis of the katcin fusion protein in a monkey. The monkey was sensitized with cat allergic serum plus different doses of katcin or human IgE. After 4 hours, the monkey was intravenously challenged with purified Fel d1 plus Evans blue. Cutaneous anaphylaxis was assessed visually by the blue dye leakage from blood vessels into the skin.

DETAILED DESCRIPTION OF THE INVENTION

The present invention provides fusion proteins capable of cross-linking an Fc receptor for an IgE (e.g., FcεR1) and an IgG inhibitory receptor that contains an IMIT (e.g., FcγRIIb), thereby inhibiting the IgE-driven mediators released from mast cells and basophils. In addition, the present invention provides nucleic acid molecules encoding the fusion proteins, vectors and host cells for producing the fusion proteins, pharmaceutical compositions comprising the fusion proteins, and methods for ameliorating or reducing the risk of IgE-mediated allergic diseases or other disorders.

In one aspect, the present invention provides a fusion protein comprising (i) a first polypeptide sequence capable of specifically binding to a native IgE molecule, (ii) a second polypeptide sequence capable of specifically binding to a native IgG inhibitory receptor comprising an immune receptor tyrosine based inhibitory motif (ITIM), and (iii) an IgG hinge region, wherein the first polypeptide sequence comprises an allergen sequence, and wherein the first polypeptide sequence and the second polypeptide sequence is functionally connected via the IgG hinge region. Because by specifically binding to the native IgE molecule, the first polypeptide is indirectly bound to an IgE receptor for the native IgE molecule (e.g., FcϵRI receptor) via the native IgE molecule, the fusion protein is capable of cross-linking the IgE receptor with the IgG inhibitory receptor.

The term "immunoglobulin (Ig)" refers to the immunity-conferring portion of the globulin proteins of serum, and to other glycoproteins that have the same functional characteristics.

The term "IgG" refers to one of Ig isotypes found in serum, which is the main antibody raised in response to an antigen and has four major subtypes, $IgG_1$, $IgG_2$, $IgG_3$ and $IgG_4$.

The term "IgE" refers to one of Ig isotypes found in serum, which binds tightly to mass cell and basophils, and when additionally bound to antigen, causes release of histamine and other mediators of immediate hypersensitivity. This isotype of Ig plays a primary role in allergic reactions such as hay fever, asthma and anaphlaxis.

Immunoglobulin sequences, including their heavy chain constant regions, are well known in the art (see, Kabat et al., Sequences of Proteins of Immunological Interest, $5^{th}$ Ed. Public Health Service, National Institute of Health, Bethesda, Md., 1991). Additional references include Ellison et al., Nucl. Acid Res. 10:4071-4079, 1982 (for the human $IgG_1$ heavy chain constant region); Takahashi et al., Cell 29:671-679, 1982 (for the human $IgG_1$, $IgG_2$, $IgG_3$, and $IgG_4$ heavy chain constant regions); Krawinkel et al., EMBO J. 1:403-407, 1982 (for the human $IgG_2$, $IgG_3$, $IgG_4$ heavy chain constant regions); Ellison et al., Proc. Nat. Acad. Sci. USA 79:1984-1988, 1982 (for the human $IgG_2$ heavy chain constant region); Ellison et al., DNA 1:11-18, 1982 (for the human $IgG_4$ heavy chain constant region); Max et al., Cell 29:691-699, 1982 (for the human IgE heavy chain constant region); Saxon et al., J. Immunol. 147:4000, 1991 (for IgE isoforms); Peng et al., J. Immunol. 148:129-136, 1992 (for IgE isoforms); Zhang et al., J. Exp. Med. 176:233-243, 1992 (for IgE isoforms); and Hellman, Eur. J. Immunol. 23:159-167, 1992 (for IgE isoforms).

The term "inhibitory receptor" refers to a receptor capable of down regulating a biological response mediated by another receptor.

The term "immune receptor tyrosine based inhibitory motif (ITIM)" refers to a motif generally represented by the formula Val/Ile-Xaa-pTyr-Xaa-Xaa-Leu/Val, where Xaa represents any amino acid.

The term "IgG inhibitory receptor" refers to a member of the inhibitory receptor superfamily capable of attenuating an FcϵR-mediated response.

The term "IgG inhibitory receptor comprising an ITIM" refers to an IgG inhibitory receptor that contains an ITIM. Exemplary IgG inhibitory receptors include low-affinity FcϵRIIb receptor and gp49b1.

A "native" protein (e.g., an immunoglobulin protein or its receptor) refers to a naturally occurring protein.

A polypeptide specifically binds to another polypeptide (e.g., a native IgE molecule or a native IgG inhibitory receptor) if it binds to the other polypeptide with a binding constant of at least $10^6M^{-1}$ (e.g., $10^7M^{-1}$, $10^8M^{-1}$, $10^9M^{-1}$, and $10^{10}M^{-1}$).

The term "allergen" refers to specific antigens capable of inducing IgE-mediated allergies. Exemplary allergens include those found in food, pollen, house dust, and dander from house pets.

As indicated above, the first polypeptide sequence of the fusion protein comprises an allergen sequence. The allergen sequence may be a naturally occurring allergen sequence, a portion of a naturally occurring allergen sequence, or a variant of a naturally occurring allergen sequence, that is capable of specifically binding to an allergen-specific IgE molecule.

In certain embodiments, the first polypeptide sequence comprises an allergen sequence with an at least 80%, 85%, 90%, 95%, or 99% sequence identify with a naturally occurring allergen sequence or a portion thereof that is capable of binding to an allergen-specific IgE molecule.

"Sequence identity" is defined as the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values are generated by the NCBI BLAST2.0 software as defined by Altschul et al., (1997), "Gapped BLAST and PSI-BLAST: a new generation of protein database search programs", Nucleic Acids Res., 25:3389-3402 with the parameters set to default values.

The sequences of a large number of allergens are known in the art. Exemplary allergens include mite allergen Der p1 (see, SEQ ID NOS:3 and 4 for its nucleotide and amino acid sequences), cat allergen Fel d1 (see, SEQ ID NOS:5 and 6 for the nucleotide and amino acid sequences of its chain 1, and SEQ ID NOS:7 and 8 for the nucleotide and amino acid sequences of its chain 2), and peanut allergen Ara h (see, SEQ ID NOS:9 and 10 for its nucleotide and amino acid sequences). Numerous other allergens and their sequences are available from the SWISS-PROT database, some of which are listed in Table 1 of U.S. Patent Application Publication No. US 2003/0082190 (which is incorporated herein by reference).

In certain embodiments, the first polypeptide sequence of the fusion protein of the present invention comprises native cat allergen Fel d1 or a portion thereof. For example, in certain embodiments, the first polypeptide sequence comprises both a portion of native cat allergen Fel d1 chain 1 as set forth in SEQ ID NO:18 and a portion of native cat allergen Fed d1 chain 2 as set forth in SEQ ID NO:19.

In certain embodiments, the first polypeptide sequence of the fusion protein of the present invention comprises a sequence having an at least 80%, 85%, 90%, 95%, or 99% sequence identity with native cat allergen Fel d1 or a portion thereof and capable of specifically binding to a cat allergen Fel d1-specific IgE antibody.

In certain embodiments, the first polypeptide sequence of the fusion protein of the present invention comprises both a sequence having an at least 80%, 85%, 90%, 95%, or 99% sequence identity with native cat allergen Fel d1 chain 1 and another sequence having an at least 80%, 85%, 90%, 95%, or 99% sequence identity with native cat allergen Fel d1 chain 2, wherein the first polypeptide is capable of specifically binding to a cat allergen Fel d1-specific IgE antibody.

In certain embodiments, the first polypeptide sequence of the fusion protein of the present invention comprises native mite allergen protein Der p1 as set forth in SEQ ID NO:4 or a portion thereof.

In certain embodiments, the first polypeptide sequence of the fusion protein of the present invention comprises a sequence having an at least 80%, 85%, 90%, 95%, or 99% sequence identity with native mite allergen protein Der p1 set forth in SEQ ID NO:4 or a portion thereof and capable of specifically binding to a mite allergen protein Der p1-specific IgE antibody.

In certain embodiments, the first polypeptide sequence of the fusion protein of the present invention comprises native peanut allergen Ara h as set forth in SEQ ID NO:10 or a portion thereof.

In certain embodiments, the first polypeptide sequence of the fusion protein of the present invention comprises a sequence having an at least 80%, 85%, 90%, 95%, or 99% sequence identity with native peanut allergen Ara h as set forth in SEQ ID NO:10 or a portion thereof and capable of specifically binding to a peanut allergen Ara h-specific IgE antibody.

The second polypeptide sequence in the fusion protein of the present invention is capable of specifically binding to a native IgG inhibitory receptor comprising an ITIM, such as FcγRIIb receptor and gp49b1.

In certain embodiments, the second polypeptide sequence comprises the CH2 and CH3 portion of human IgG immunoglobulin heavy chain constant region. In certain embodiments, the second polypeptide sequence comprises the CH2 and CH3 portion of human $IgG_1$ immunoglobulin heavy chain constant region as set forth in SEQ ID NO:21. In certain other embodiments, the second polypeptide sequence comprises the CH2 and CH3 portion of human $IgG_2$, $IgG_3$, or $IgG_4$ immunoglobulin heavy chain constant region.

In certain embodiments, the second polypeptide sequence comprises a sequence having an at least 80%, 85%, 90%, 95%, or 99% sequence identity with the CH2 and and CH3 portion of human IgG immunoglobulin heavy chain constant region. In certain embodiments, the second polypeptide sequence comprises having an at least 80%, 85%, 90%, 95%, or 99% sequence identity with the CH2 and CH3 portion of human $IgG_1$ immunoglobulin heavy chain constant region as set forth in SEQ ID NO:21 and capable of specifically binding to a native IgG inhibitory receptor containing an ITIM (e.g., FcεRIIb). In certain other embodiments, the second polypeptide sequence comprises a sequence having an at least 80%, 85%, 90%, 95%, or 99% sequence identity with the CH2 and CH3 portion of human $IgG_2$, $IgG_3$, or $IgG_4$ immunoglobulin heavy chain constant region and capable of specifically binding to a native IgG inhibitory receptor containing an ITIM (e.g., FcεRIIb).

The first and second polypeptides of the fusion protein of the present invention are functionally connected via an IgG hinge region.

The term "IgG hinge region" refers to the hinge region of a native IgG immunoglobulin heavy chain constant region, a portion of the hinge region of a native IgG immunoglobulin heavy chain constant region that consists of at least 10 consecutive amino acid residues (e.g., 10, 11, 12, 13, or 14 amino acid residues), or a sequence that has an at least 80% (e.g., 80%, 85%, 90%, 95%, or 99%) sequence identity with the hinge region of a native IgG immunoglobulin heavy chain constant region or a portion thereof that consists of at least 10 consecutive amino acid residues (e.g., 10, 11, 12, 13, or 14 amino acid residues).

The first polypeptide of the fusion protein of the present invention is "functionally connected" to the second polypeptide if in the resulting fusion protein, the first polypeptide is still capable of specifically binding to a native IgE molecule, and the second polypeptide is still capable of specifically binding to a native IgG inhibitory receptor comprising an ITIM.

In certain embodiments, the first and second polypeptides of the fusion protein of the present invention are functionally connected via the hinge region of an $IgG_1$ immunoglobulin. For example, the first and second polypeptides may be functionally connected via the 15 amino acid hinge region of human $IgG_1$ immunoglobulin as set forth in SEQ ID NO:20.

In certain embodiments, the first and second polypeptides of the fusion protein of the present invention are functionally connected via a portion of the hinge region of an $IgG_1$ immunoglobulin (e.g., human $IgG_1$ immunoglobulin) that consist of at least 10, 11, 12, 13, or 14 amino acid residues.

In certain embodiments, the first and second polypeptides of the fusion protein of the present invention are functionally connected via a sequence having an at least 80%, 85%, 90%, 95%, 99% of the hinge region of an $IgG_1$ immunoglobulin (e.g., human $IgG_1$ immunoglobulin) or a portion thereof that consists of at least 10 consecutive amino acid residues (e.g., 10, 11, 12, 13, or 14 amino acid residues).

In certain embodiments, the first and second polypeptides of the fusion protein of the present invention are functionally connected via the hinge region of an $IgG_2$, $IgG_3$, or $IgG_4$ immunoglobulin. For example, the first and second polypeptides may be functionally connected via the hinge region of human $IgG_2$, $IgG_3$, or $IgG_4$ immunoglobulin as set forth in SEQ ID NO:22, 23, or 24.

In certain embodiments, the first and second polypeptides of the fusion protein of the present invention are functionally connected via a portion of the hinge region of an $IgG_2$, $IgG_3$, or $IgG_4$ immunoglobulin (e.g., human $IgG_2$, $IgG_3$, or $IgG_4$ immunoglobulin) that consist of at least 10, 11, 12, 13, or 14 amino acid residues.

In certain embodiments, the first and second polypeptides of the fusion protein of the present invention are functionally connected via a sequence having an at least 80%, 85%, 90%, 95%, 99% of the hinge region of an $IgG_2$, $IgG_3$, or $IgG_4$ immunoglobulin (e.g., human $IgG_2$, $IgG_3$, or $IgG_4$ immunoglobulin) or a portion thereof that consists of at least 10 consecutive amino acid residues (e.g., 10, 11, 12, 13, or 14 amino acid residues).

In certain embodiments, the first and second polypeptides of the fusion protein of the present invention may be linked with an IgG hinge region so that the first polypeptide is located N-terminus to the second polypeptide. In certain other embodiments, the first polypeptide may be linked to the second polypeptide via an IgG hinge region so that it is C-terminus to the second polypeptide.

In certain embodiments, the fusion proteins of the present invention is capable of (1) indirect binding of a native high-affinity FcεR1 receptor via directly binding between a native IgE molecule to which the native high-affinity FcεR1 receptor binds and the first polypeptide sequence in the fusion protein, and (2) direct binding of a native low-affinity FcγRIIb receptor via the second polypeptide sequence in the fusion protein.

Figure 1:
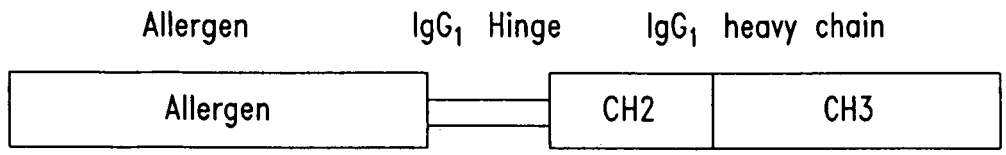

In certain embodiments, the fusion protein of the present invention comprises an allergen sequence and the CH2 and CH3 portion of human $IgG_1$ heavy chain constant region linked by the hinge region of human $IgG_1$ heavy chain constant region (see, FIG. 1). The cDNA sequence encoding the hinge-CH2—CH3 portion of the human $IgG_1$ heavy chain constant region and the amino acid sequence of this portion of the human $IgG_1$ heavy chain constant region are set forth in SEQ ID NOS:1 and 2, respectively.

Figure 2:
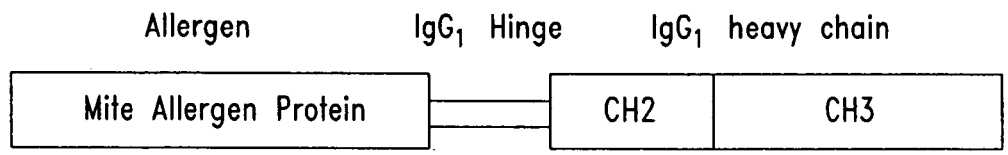

In certain embodiments, the fusion protein of the present invention comprises mite allergen protein (or a portion thereof) and the CH2 and CH3 portion of human $IgG_1$ heavy chain constant region linked by the hinge region of human $IgG_1$ heavy chain constant region (see, FIG. 2).

Figure 3:
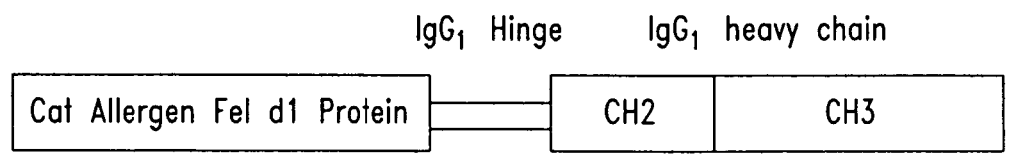

In certain embodiments, the fusion protein of the present invention comprises cat allergen Fel d1 protein (or a portion thereof) and the CH2 and CH3 portion of human $IgG_1$ heavy chain constant region linked by the hinge region of human $IgG_1$ heavy chain constant region (see, FIG. 3).

Figure 4:
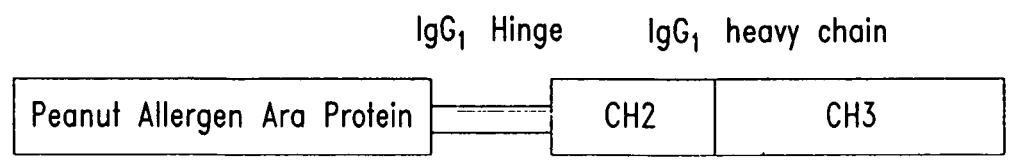
FIG. 4 illustrates the structure of an exemplary peanut allergen vaccine protein.

In certain embodiments, the fusion protein of the present invention comprises peanut allergen Ara protein (or a portion thereof) and the CH2 and CH3 portion of human $IgG_1$ heavy chain constant region linked by the hinge region of human $IgG_1$ heavy chain constant region (see, FIG. 4).

The fusion proteins of the present invention are capable of specific binding of a native IgE molecule via its first polypeptide and specific binding of a native IgG inhibitory receptor comprising an ITIM via its second polypeptide. Such specific binding may be tested using any known assays, such as competitive binding assays including RIAs and ELISAs. Protein-protein complexes (e.g., complexes formed between the fusion protein and a native IgE molecule, between the fusion protein and a native IgG inhibitory receptor comprising an ITIM, and among the fusion protein, a native IgE molecule, and a native IgG inhibitory receptor comprising an ITIM) can be identified and isolated using various methods such as filtration, centrifugation, and flow cytometry. The assays may be performed using a purified protein of interest (e.g., a first or second polypeptide sequence of a fusion protein of the present invention, a fusion protein of the present invention, a native IgE molecule, or a native IgG inhibitory receptor comprising an ITIM), intact cells expressing a protein of interest, or cell lysate containing a protein of interest. The protein of interest may be immobilized or labeled prior to or during the assays.

The fusion proteins of the present invention may be prepared using standard techniques of recombinant DNA technology.

In a related aspect, the present invention provides a nucleic acid molecule comprising a nucleotide sequence encoding the fusion proteins described herein. In certain embodiments, the nucleic acid molecule comprises a nucleotide sequence encoding a fusion protein that comprises an allergen sequence capable of specifically binding to a native IgE molecule functionally linked to a second polypeptide sequence capable of specifically binding to a native IgG inhibitory receptor comprising an ITIM (e.g., FcϵRIIb) via an IgG hinge region.

In certain embodiments, the nucleic acid molecule comprises a nucleotide sequence encoding a fusion protein that comprises a native allergen polypeptide sequence or a portion thereof linked to the CH2—CH3 portion of human $IgG_1$ heavy chain constant region via the hinge region of human $IgG_1$ heavy chain constant region.

In certain embodiments, the nucleic acid molecule comprises a nucleotide sequence encoding the katcin fusion protein that comprises a portion of cat allergen Fel d1 and the hinge-CH2—CH3 portion of human IgG1 as set forth in SEQ ID NO:17.

In certain embodiments, the nucleic acid molecule comprises a nucleotide sequence encoding the katcin fusion protein and has a nucleotide sequence as set forth in SEQ ID NO:16.

In certain embodiments, the nucleic acid molecule comprises a nucleotide sequence encoding a fusion protein of the present invention and is capable of specifically binding to SEQ ID NO:16 or its full length complement under stringent hybridization and wash conditions.

"Stringent hybridization and wash conditions" are defined as hybridization in 50% formamide, 6×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (100 μg/ml), 0.5% SDS, and 10% dextran sulfate at 42° C. for at least 12 hours, with washes in 2×SSC (sodium chloride/sodium citrate) containing 0.1% SDS at 42° C. for 30 minutes twice and 0.2×SSC containing 0.1% SDS at 42° C. for 30 minutes.

The nucleic acid molecules encoding the fusion proteins of the present invention may be obtained via standard recombinant DNA techniques, chemical synthesis, or the combination thereof. For example, the coding sequences of various portions of the fusion proteins (e.g., first and second polypeptide sequences, and IgG hinge regions) may be obtained from natural sources or synthesized. Such sequences may be appropriately linked to produce the nucleic acid molecules encoding the fusion proteins of the present invention using various commercially available cloning and/expression vectors (e.g., those available from companies such as Invitrogen, San Diego, Calif.).

In certain embodiments, the present invention provides vectors comprising and capable of expressing the nucleotide sequences encoding the fusion proteins described herein. In certain embodiments, the vector comprises a nucleic acid sequence encoding the katcin fusion protein as set forth in SEQ ID NO:17. In certain embodiments, the vector comprises a nucleic acid sequence encoding the katcin fusion protein and has a nucleotide sequence as set forth in SEQ ID NO:16.

The vectors of the present invention include those useful for recombinant production in *E. coli*, *S. cerevisiae* strains of yeast, a baculovirus expression system for production in insect cells, fungal cells, avian cells, mammalian cells such as Chinese Hamster Ovary cells, and plant cells.

In one aspect, the present invention provides host cells transformed with the vectors described herein. Host cells useful for transformation with the vectors of the present invention include prokaryotic and eukaryotic host cells such as bacterial cells (e.g., *E. coli* cells), yeast cells (e.g., *S. cerevisiae* cells), insect cells, fungal cells, insect cells, mammalian cells, avian cells, and cells of higher plants.

Construction of expression systems suitable for desired hosts are known in the art. For recombinant production of the fusion protein of the present invention, the DNA encoding the fusion protein is suitably ligated into the expression vector of choice and then used to transform the compatible host. The transformed host cells are then cultured and maintained under conditions appropriate for expression of the foreign gene. The fusion protein of the present invention thus produced is recovered from the culture, either by lysing the cells or from the culture medium as appropriate and known in the art. Such fusion protein may be further purified if needed using standard techniques known in the art.

Alternatively, the fusion proteins of the present invention may be produced by chemical synthesis. Such methods are well known in the art and employ either solid or solution phase synthesis methods. Information about chemical synthesis of proteins may be found, for example, in Stewart and Young, Solid Phase Peptide Synthesis, 2nd Ed., Pierce Chemical Co., Rockford, Ill., 1984; Barany and Merrifield, The Peptide: Analysis Synthesis, Biology, editors E. Gross and J. Meienhofer, Vol. 2, Academic Press, New York, 1980; and Bodansky, Principles of Peptide Synthesis, Springer-Verlag, Berlin, 1984.

In one aspect, the present invention provides pharmaceutical compositions that comprise the fusion proteins of the present invention and pharmaceutically acceptable ingredients, such as physiologically acceptable excipients, additives, carriers or diluents. Suitable physiological acceptable ingredients are described in Remington's Pharmaceutical Sciences, 18$^{th}$ Edition, Mack Publishing Co., Easton, Pa., 1990. Additional exemplary physiological acceptable ingredients include coloring, stabilizing agents, osmotic agents, and antibacterial agents.

The fusion proteins of the present invention may be used as vaccines, and thus also referred to as "allergen vaccine proteins." Accordingly, in one aspect, the present invention provides methods for ameliorating or reducing the risk of an IgE-mediated allergic disease, comprising administering to a patient in need thereof an effective amount of the fusion proteins described herein. In certain embodiments, the present invention provides a method for ameliorating or reducing the risk of cat allergy, comprises administering to a patient in need thereof an effective amount of the katcin fusion protein with the amino acid sequence as set forth in SEQ ID NO:17.

A disease is "ameliorated" if the symptoms of the disease are alleviated, the extent of the disease is diminished, the progression of the disease is delayed or slowed, the disease state is ameliorated or palliated, and/or partial or total remission occurs.

The risk of a disease is "reduced" if the likelihood of a patient to have the disease is reduced, or the onset of the disease in a patient is delayed.

A "patient in need" refers to a patient already with an allergic disease or is prone to have an allergic disease. The patient may be a human or a non-human mammalian subject.

An "effective amount" is an amount sufficient to effect beneficial or desired therapeutic (including preventive) results. An effective amount can be administered in one or more administrations.

The IgE-mediated allergic diseases that the fusion proteins of the present invention are useful in ameliorating or reducing the risk of the diseases include, but are not limited to, allergic asthma, allergic rhinitis, hay fever, food allergy, such as those caused by peanut or other nuts, shellfish, milk, fish, soy, wheat, and egg, atopic dermatitis, pet allergy (e.g., cat allergy and dog allergy), eczema, drug allergy, chronic urticaria, ear infections associated with allergy, angioedema, allergy caused by pollen, mold, dust mite droppings, insect stings, or cockroaches or other insects, and anaphylactic shock.

The fusion proteins or pharmaceutical compositions of the present invention may be administered by any means that enables the fusion proteins to reach the targeted cells. These methods include, but are not limited to, oral, topical, transdermal, subcutaneous, intravenous, intramuscular, intra-arterial, intranasal, intrapulmonary, and intraparenteral modes of administration. The fusion proteins may be administered singularly or in combination with other compounds useful for anti-IgE therapy or allergen immunotherapy.

In certain embodiments, the fusion proteins or pharmaceutical compositions of the present invention are administered by inhalation. In certain other embodiments, the fusion proteins or pharmaceutical compositions of the present invention are administered by injection.

For parenteral administration, the fusion proteins of the invention can be, for example, formulated as a solution, suspension, emulsion or lyophilized powder in association with a physiologically acceptable parenteral vehicle such as water, saline, Ringer's solution, dextrose solution, and 5% human serum albumin. Liposomes and nonaqueous vehicles such as fixed oils may also be used. For example, a parenteral composition suitable for administration by injection is prepared by dissolving 1.5% by weight of active ingredient in 0.9% sodium chloride solution. The compositions of the present invention may be administered as a single dose or in multiple doses.

The compositions of the present invention may be provided in the form of an oral liquid, tablet, or capsule, nasal spray, aerosol, suspension, solution, emulsion, and/or eye drop. The appropriate dosage can be extrapolated from the dosages that indicate efficacy in vitro or in animal studies. The dosage administered varies depending upon factors such as: pharmacodynamic characteristics; its mode and route of administration; age, health, and weight of the recipient; nature and extent of symptoms; type of concurrent treatment; and frequency of treatment. Usually, the dosage of the fusion protein can be about 0.01 to 100 mg/kg of body weight, such as about 0.1 to 100, 0.05 to 50, or 1.0 to 10 mg/kg of body weight. The fusion proteins or pharmaceutical compositions may be administered to an individual per day in divided doses one or more times per day to obtain desired results.

The following example is provided for illustration of, not for limitation to, the present invention.

EXAMPLE

Construction of Katcin Fusion Protein

The human genomic IgG$_1$ DNA was obtained by using polymerase chain reaction. More specifically, human B cells were purified from peripheral blood and the genomic IgG$_1$ DNA was isolated and used as the template for a polymerase chain reaction. The 5'-end primer for IgG$_1$ Fc region is 5'-GG GGATCC GAG CCC AAA TCT TGT GAC-3' (SEQ ID NO:11), containing a BamH I site, and 3'-end primer is 5'-GT GCGGCCGC TCA TTT ACC CGG AGA CAG GGA GAG-3' (SEQ ID NO:12), containing a Not I site. After amplification, the PCR product was cloned into pCR4-TOPO vector (Invitrogen) and the sequences were confirmed. Nucleotide sequence analysis of the clones revealed that they contained full-length IgG$_1$ Fc genomic DNA from the hinge to CH3. These sequences matched the genomic DNA sequence of the corresponding region of human IgG$_1$ in the GenBank database (SEQ ID NO:15). The human IgG$_1$ Fc genomic DNA fragment was then subcloned into pSecTag2 (Invitrogen) vector.

The cat allergen Fel d1 cDNA was obtained by reverse transcription PCR. mRNA was prepared from cat epithelial cells and after reverse transcription, the resulting cDNA was used as template for PCR. The 5'-end primer for the PCR reaction is 5'-GGCCCAGCCGGCC GAA ATT TGC CCA GCC GTG-3' (SEQ ID NO:13), containing a Sfi I site, and 3'-end primer for the PCAT reaction is 5'-GGATCC TCT CCC CAA AGT GTT CAG-3' (SEQ ID NO:14), containing a BamH I site. The PCR products were cloned into pCR4-TOPO vector (Invitrogen) and the sequences were confirmed.

The Fel d1 cDNA was subcloned into pSecTag2 vector (Invitrogen) and fused with the human IgG$_1$ Fc genomic DNA fragment. The resulting construct encodes the protein katcin. The nucleotide sequence encoding katcin and the amino acid sequence of katcin are set forth in SEQ ID NOS:16 and 17, respectfully. The katcin protein comprises from its N-terminus to its C-terminus: a leader sequence, a portion of Fel d1 chain 1 (as set forth in SEQ ID NO:18), a linker sequence, a portion of Fel d1 chain 2 (as set forth in SEQ ID NO:19), IgG$_1$ hinge (as set forth in SEQ ID NO:20), and IgG$_1$ CH2-CH3 (as set forth in SEQ ID NO:21).

The expression vector containing the nucleic acid sequence encoding katcin was transfected into CHO-k1 cells (ATCC). After selection with 500 ug/ml of Zeocin (Invitrogen), a stable expression cell line expressing the katcin fusion protein was obtained. The katcin fusion protein was purified from the cell culture supernatants by using protein A affinity chromatography (Amersham Pharmacia).

Western Blot Analysis of Katcin Fusion Protein

Katcin fusion proteins were purified from several clones (HC1, HC2, HC3, HC4, HC10, and HC20) and mixed with standard SDS-PAGE loading buffer (Invitrogen) that containing protease inhibitors (1 μg/ml leupeptin, 1 μg/ml aprotinin, and 2 mM phenylmethylsulfonyl fluoride). Protein concentrations were determined using a Bio-Rad protein assay. 10 μg fusion proteins purified from various clones were subjected to SDS-PAGE under reducing condition, and then transferred to nitrocellulose membranes. The membranes were incubated with primary antibody (anti-Fel d1 monoclonal antibody) after blocking with 10% non-fat milk followed by incubation with horseradish peroxidase-conjugated anti-mouse secondary antibody. Visualization was performed using the chemiluminescence detection solution and analysis by X cell sure Lock tm Electrophoresis cell.

Figure 5:
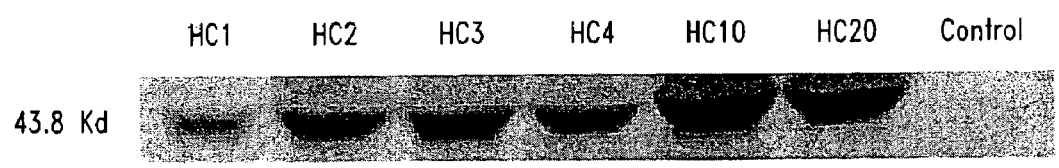
FIG. 5 is a photograph that shows the results of a Western blot analysis of katcin fusion proteins purified from different clones that were probed with mouse anti-Fel d1 monoclonal antibody and goat anti-mouse antidody conjugated with horseradish peroxidase.

The results (FIG. 5) show that katcin proteins purified from various clones were of the expected molecular weight and were specific to the anti-Fel d1 antibody.

ELISA Assay for Katcin Binding Specificity for Fel D1 and IgG Fcr

100 μl of 1:500 dilution of anti-Fel d1 antibody (200 μg/ml) (100 μL/well) was incubated per well in flat-bottomed 96-well microliter plates overnight at 4° C. Plates were washed three times with phosphate-buffered saline (PBS), and blocked with PBS containing 0.01% Tween-20 (PBST) at room temperature (RT) for 2 h. Plates were then incubated with 100 μL/well of katcin protein at 4° C. overnight, washed three times with PBST, incubated with 100 μL alkaline phosphatase-conjugated goat anti human IgG Fc antibody for 2 hours at room temperature and then washed four times with PBST. Bound proteins were detected using BluePhos Microwell Phosphatase substrate (KPL, manufacturer's directions) and analyzed using a μQuant (Biotek, Winooski, Vt.) plate reader at 450 nm. Values represent the mean of triplicate experiments.

Figure 6:
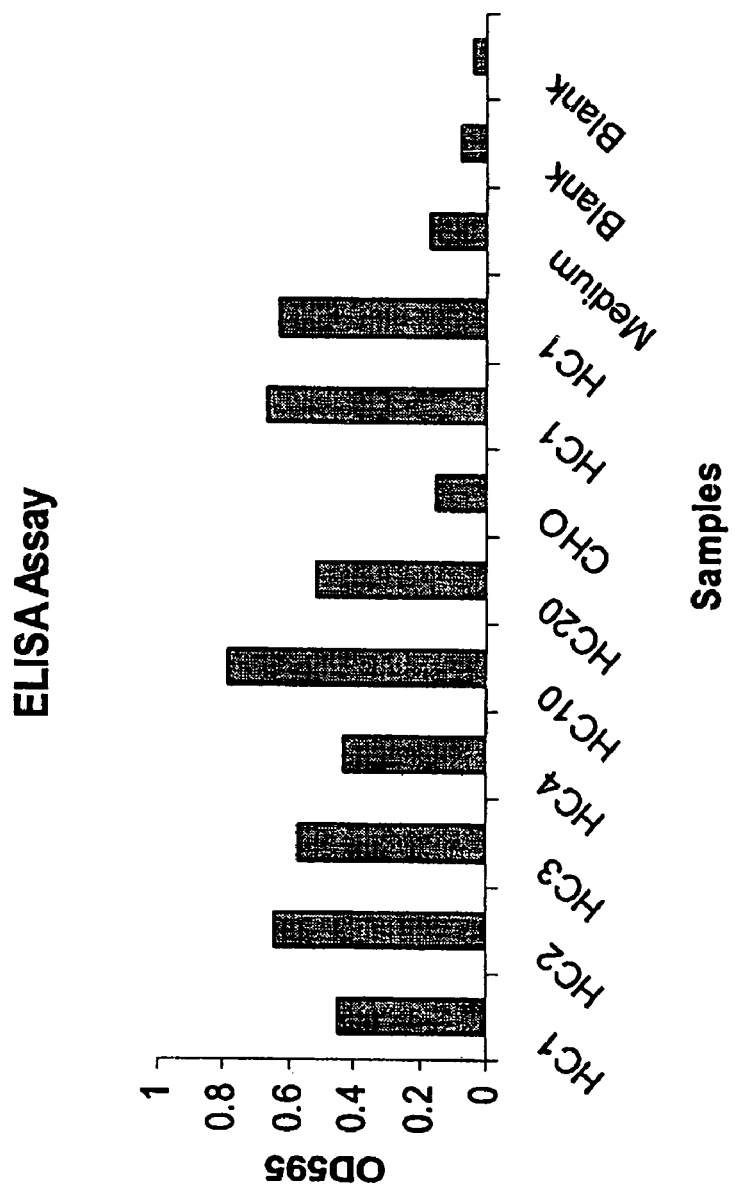
FIG. 6 is a graph that shows the results of an ELISA analysis of katcin fusion proteins purified from different clones. The purified proteins were loaded into a plate coated with mouse anti-Fel d1 antibody and detected with alkaline phosphatase-conjugated goat anti-human IgG Fc antibody.

The results (FIG. 6) show that katcin proteins were correctly expressed in various clones and cound be recognized by anti-Fel D1 and anti-human IgG antibodies.

Inhibition of Passive Cutaneous Anaphylaxis (PCA) by Katcin in Monkey

A monkey was intradermally sensitized on the leg skin by cat allergy patient serum (Plasma International Inc) plus different doses of katcin fusion protein or control human myeloma IgE. Four hours later, the animal was intravenously given 10 μg of purified Fel d1, plus 5 ml of 0.5% Evans Blue dye. Sites were photographed 30 minutes later and largest diameter of bluing measured.

The results (FIG. 7) show that katcin specifically inhibited cat serum-induced IgE-medicated allergic reaction in vivo.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A fusion protein comprising (i) a first polypeptide sequence capable of specifically binding to a native IgE molecule, (ii) a second polypeptide sequence capable of specifically binding to a native IgG inhibitory receptor comprising an immune receptor tyrosine based inhibitory motif (ITIM), and (iii) an IgG hinge region, wherein the first polypeptide sequence comprises an allergen sequence, the first polypeptide sequence and the second polypeptide sequence is functionally connected via the IgG hinge region, and the fusion protein comprises the amino acid sequence as set forth in SEQ ID NO:17.

2. A pharmaceutical composition comprising the fusion protein of claim 1 and a pharmaceutically acceptable ingredient.

* * * * *